United States Patent
Dal Molin et al.

(10) Patent No.: US 8,255,048 B2
(45) Date of Patent: Aug. 28, 2012

(54) CIRCUIT FOR CONTROLLED COMMUTATION OF MULTIPLEXED ELECTRODES FOR AN ACTIVE IMPLANTABLE MEDICAL DEVICE

(75) Inventors: Renzo Dal Molin, Chatillon (FR); Alain Ripart, Chatillon (FR)

(73) Assignee: Sorin CRM S.A.S., Clamart (FR)

( * ) Notice: Subject to any disclaimer, the term of this patent is extended or adjusted under 35 U.S.C. 154(b) by 876 days.

(21) Appl. No.: 11/965,432

(22) Filed: Dec. 27, 2007

(65) Prior Publication Data

US 2008/0177343 A1 Jul. 24, 2008

(30) Foreign Application Priority Data

Dec. 28, 2006 (FR) ..................................... 06 11478

(51) Int. Cl.
*A61N 1/00* (2006.01)
(52) U.S. Cl. .................. 607/9; 607/30; 607/31; 607/60; 607/61; 607/115; 607/116
(58) Field of Classification Search ...... 607/9, 115–116, 607/30–31, 60–61
See application file for complete search history.

(56) References Cited

U.S. PATENT DOCUMENTS

| | | | |
|---|---|---|---|
| 4,532,930 A | 8/1985 | Crosby et al. | |
| 4,793,353 A | 12/1988 | Borkan | |
| 5,470,348 A | 11/1995 | Neubauer et al. | |
| 5,649,970 A * | 7/1997 | Loeb et al. | 607/57 |
| 5,755,747 A * | 5/1998 | Daly et al. | 607/55 |
| 6,418,348 B1 | 7/2002 | Witte et al. | |
| 2002/0169484 A1 | 11/2002 | Mathis | |
| 2003/0149456 A1 | 8/2003 | Rottenberg et al. | |
| 2004/0172104 A1* | 9/2004 | Berg et al. | 607/60 |
| 2004/0220650 A1 | 11/2004 | Houben et al. | |
| 2006/0058588 A1 | 3/2006 | Zdeblick et al. | |

FOREIGN PATENT DOCUMENTS

| | | |
|---|---|---|
| EP | 0 247 649 A1 | 2/1987 |
| EP | 1 062 969 A | 12/2000 |

* cited by examiner

*Primary Examiner* — Nicole F Lavert
(74) *Attorney, Agent, or Firm* — Orrick Herrington & Sutcliffe, LLP

(57) ABSTRACT

A circuit for controlled commutation of multiplexed electrodes, for an active implantable medical device. This circuit is located in a lead equipped with multiplexed sensing/pacing electrodes. This circuit decodes a signal generated by a generator, commanding a series of switches, which ensures selective coupling of the various electrodes to the proximal and distal terminals of the generator. This signal is a modulated signal comprising a coded series of logic pulses defining a particular configuration for coupling the lead electrodes to the proximal or distal terminal of the generator. The signal comprises a micropulse, that precedes the coded series of logic pulses and has an amplitude and duration lower than the amplitude and duration of each of the logic pulses. The detection of this micropulse activates, in response, all the circuit switches to an open position over a duration (PHASE 1) at least equal to the duration of reception of the coded series of logic pulses.

14 Claims, 4 Drawing Sheets

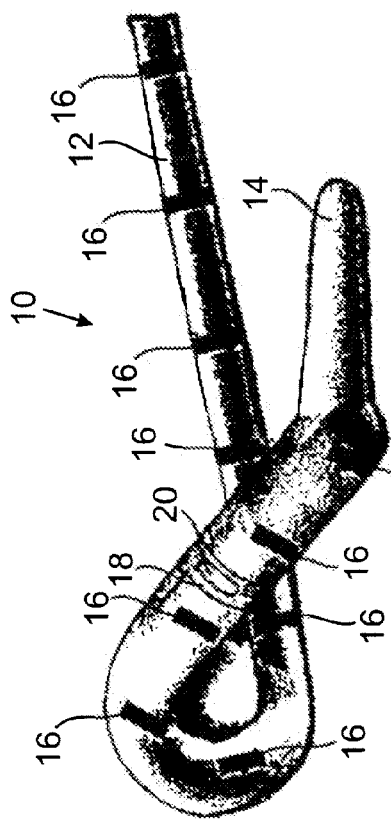
FIG. 1
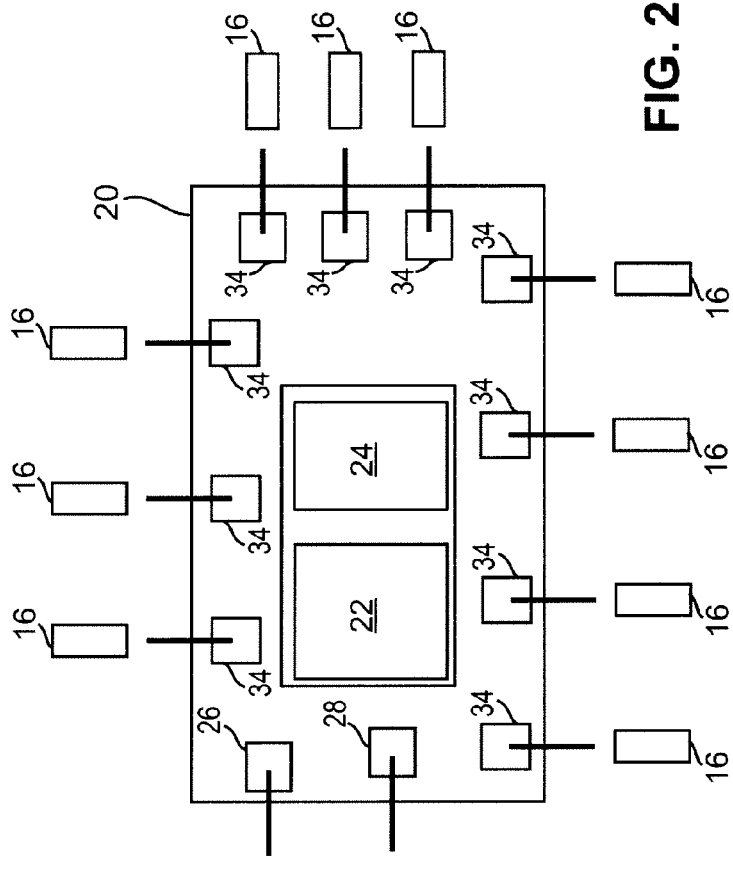
FIG. 2
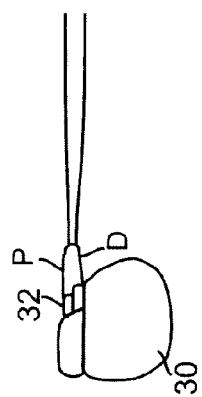

CIRCUIT FOR CONTROLLED COMMUTATION OF MULTIPLEXED ELECTRODES FOR AN ACTIVE IMPLANTABLE MEDICAL DEVICE

FIELD OF THE INVENTION

The present invention relates to "active medical devices" as such devices are defined by the Jun. 14, 1993 Directive 93/42/CE of the Counsel of the European Community, and more particularly to "active implantable medical devices" as defined by the Jun. 20, 1990 Directive 90/385/CEE of the Counsel of the European Community.

This definition particularly includes devices intended to monitor cardiac activity and schedule and deliver pulses for pacing, resynchronizing, defibrillating and/or cardioverting the heart in response to a rhythm disorder detected by these devices. The definition also includes neurological devices, medical drug diffusion pumps, cochlear implants, implanted biological sensors, etc., as well as pH measurement devices or intracorporeal impedance measurement devices (such as transpulmonary impedance or intracardiac impedance).

BACKGROUND OF THE INVENTION

Active implantable medical devices collect signals and deliver pacing pulses through electrodes that are integrated in a lead. The lead is connected to the device's power supply and circuitry through a connector.

The electrodes are intended to contact the tissue(s) to be stimulated, or tissue(s) from which an electrical signal is to be collected; for example, myocardium, nerve, muscle, etc. In the case of a device for cardiac diagnosis and therapy, these electrodes can be endocardial electrodes (located in a cavity of myocardium and in contact with a wall thereof), epicardial electrodes (preferably, for defining a reference potential or for applying a shock), or intravascular electrodes (for example, the lead may be introduced through the coronary sinus to a location in front of the left ventricle wall).

Recent developments in the domain of so-called "multi-site" devices has increased the number of electrodes that these devices can use and now permits single or multiple stimulation and sensing sites to improve the operation of these devices.

In the particular case of ventricular resynchronization devices (so-called "CRT" devices, for Cardiac Resynchronization Therapy), referred to here in a non-limiting manner, a device equipped with electrodes to pace both ventricles must be implanted in a patient. Pacing the right ventricle (and right atrium) is performed by a standard endocardial lead. However, it is very difficult to access the left ventricle. To pace the left ventricle, usually, a lead is introduced through a coronary vein in the epicardium and the tip of the lead must be positioned in front of the left ventricle. The implanting procedure is very difficult because the diameter of the coronary vessels decreases as the lead progresses and it is not easy to find the optimal position for the lead during the implantation procedure. Further, the proximity of the lead to the phrenic nerve may result in undesirable pacing.

So-called "multi-electrode" leads have been developed to palliate these difficulties. As an example, multi-electrode leads can be equipped with ten electrodes and the lead(s) providing the best pacing can be chosen after implantation. Electrode selection may be done automatically by measuring the endocardial acceleration peaks (EAP, also referred to as PEA), measuring bioimpedance, or based upon any other kind of sensor likely to provide information on the hemodynamic status of the patient. Electrode selection may also be done "by hand" by the practitioner, by means of a suitable intelligent programmer communicating with the pulse generator.

Because the lead body must have a very narrow diameter, it is not possible to embed as many conductors as electrodes within the lead because the lead would be unacceptably wide. The diameter of the lead is important for the lead itself and also so that the connector can be level with the pulse generator.

For these reasons, systems of electrode multiplexing have been developed to allow the multiplicity of electrodes to interface with two conductors connected to the pulse generator's terminals (the two terminals are hereinafter referred to as "distal" and "proximal", similar to the location of corresponding electrodes of a simple endocardial bipolar lead). In a simplified embodiment, these two conductors may be replaced by a single conductor (corresponding to a simple unipolar endocardial lead), in which the pulse generator's case ensures the circuit feedback, through the patient's body tissues. The particular embodiment using a single conductor can be adapted to one in which the lead comprises two conductors.

United States Published Patent Application No. US 2006/0058588, issued as, U.S. Pat. No. 7,214,189 (filed Dec. 1, 2005) describes a device in which the pulse generator is connected to a multi-electrode lead by two conductors via a multiplexer/demultiplexer circuit. These two conductors collect depolarization signals and deliver pacing pulses. The two conductors also deliver logic signals to the multiplexer/demultiplexer which provide control over the selection switches for one or more lead electrodes. These signals also deliver energy that is required for the operation of the multiplexer/demultiplexer circuit and switches.

The multiplexer/demultiplexer circuits and switches are preferably located at the lead tip. In a preferred embodiment, the commuters are micro electromechanical systems (MEMS), technologically integrable into the substrate of a chip that can be embedded within the lead body. Such components are, for example, described in United States Published Patent Application No. US 2004/0220650, issued as, U.S. Pat. No. 7,474,923 (filed Apr. 29, 2003).

In the prior art techniques, notably those disclosed in United States Published Patent Application US 2003/0149456 (abandoned), the switches are controlled by sending a coded series of logic pulses to the circuit located at the lead tip. Each sequence of pulses determines one of the switches to be set to "on" or "off" in a univalent way. However, in order for the circuit to detect that the collected signal is a coded sequence of pulses and not a pacing signal, the pulse sequence is initiated with a logic pulse sequence coding a byte to zero. Decoding of this byte allows the circuit to recognize that the signal that will follow is a command signal, and this circuit then opens all the switches so as to electrically isolate the electrodes from the pulses that will then be delivered. Once the pulse sequence has been collected and analyzed, the circuit actuates the switches according to the particular configuration corresponding to this sequence code.

This technique, however, presents a risk. When the byte defining the start of the coded pulse sequence is set to zero and applied to the circuit, the corresponding logic level is equally applied to at least one of the electrodes—the one(s) that is(are) commuted by the switches—because the switches at that time have not all been scheduled to open. This creates a risk that is not negligible for the patient because the logic levels of the pulse sequences have non-negligible levels of voltage and are likely to induce undue fibrillation, therefore creating a potentially fatal risk to the patient.

For these reasons, the technique proposed by the prior art is mainly restricted to the selection of one or many optimal electrodes at the time of implantation, but is not suited to any post implantation programming, either automatic or manual, of the configuration of commuted electrodes.

OBJECTS AND SUMMARY OF THE INVENTION

It is, therefore, an object of the present invention to propose a solution to the technical problems of the prior art by quickly opening switches and avoiding the application of an excessive voltage to the patient's heart, and therefore minimize the risk of inducing a fibrillation.

To that end, the invention broadly proposes a controlled commutation circuit of multiplexed electrodes of the general type described by United States Published Patent Application No. US 2006/0058588, issued as, U.S. Pat. No. 7,214,189 (filed Dec. 1, 2005) cited above, comprising: at least one proximal terminal and/or one distal terminal, able to be coupled to the pulse generator; a plurality of electrode terminals, able to be respectively coupled to the sensing/pacing lead electrodes; a plurality of switches, able to have either a closed position, in which a corresponding electrode terminal is connected to the proximal or distal terminal, or an open position in which this electrode is isolated from proximal and distal terminals; and command means, comprising means for receiving a modulated signal on the proximal and/or distal terminal delivered by the generator and comprising a coded series of logic pulses, and for decoding the modulated signal in order to actuate the switches according to a particular corresponding configuration of closed or open positions as defined by the modulated signal.

In a characteristic manner of this invention, the command means further comprise means for detecting a micropulse within the collected modulated signal, the micropulse preceding the coded series of logic pulses and presenting an amplitude and duration lower than the amplitude and duration of each of the coded series of logic pulses, and for actuating all switches in open position over a duration at least equal to the duration of the reception of the coded series of logic pulses.

The means for detecting the micropulse can preferably comprise a fast comparator presenting a response time less than 10 μsec.

In a preferred embodiment, the controlled commutation circuit has a plurality of distinct sub-circuits, each sub-circuit comprising a respective electrode terminal able to be connected to one of the pacing/sensing lead electrodes, as well as the switch(es) associated with this electrode terminal, and each of these sub-circuits comprises its own command means.

Another aspect of the present invention concerns a lead comprising such a circuit. The circuit is advantageously placed within the lead at the second extremity thereof, in the vicinity of the sensing/pacing electrodes. When the controlled commutation circuit is a circuit that has more than one sub-circuit, each sub-circuit is integrated into the lead body, or placed within a cavity of the lead body, disposed to be in close proximity to and facing a corresponding electrode and coupled to the conductor(s).

Yet another aspect of the present invention is directed to a generator that produces the signal as disclosed above. This generator preferably comprises means for setting the proximal and/or distal terminal in a high impedance state, prior to the delivery of the micropulse. More precisely, these means set one of the two terminals (distal or proximal) in a high impedance state, and connect the terminal not in a high impedance state other to the ground prior to delivery of the micropulse.

Finally, yet another aspect of the present invention is directed to the signal sequence as described above being considered as such.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which:

FIG. 1 is a general view of the tip of a left ventricular pacing lead with multiplexed electrodes;

FIG. 2 globally presents a circuit in accordance with a preferred embodiment of this invention with the different elements to which it is connected;

DETAILED DESCRIPTION OF THE INVENTION

Figure 3:
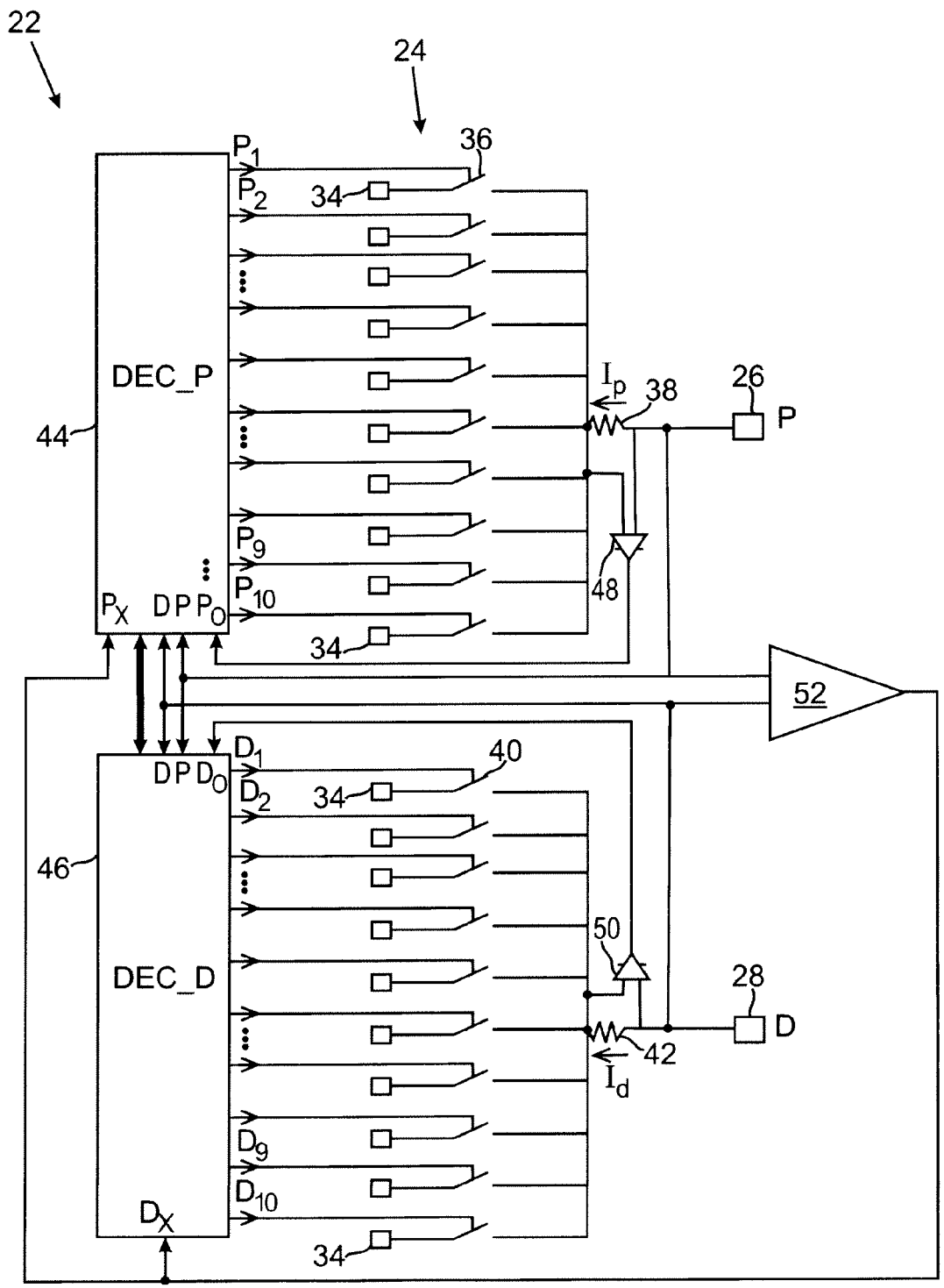
FIG. 3 is a schematic block diagram representing the main elements that constitute the circuit of this invention.

One will now describe in detail an example embodiment of the device of this invention with reference to the drawings FIGS. 1-6.

FIG. 1 schematically represents the extremity of a left ventricular pacing lead, that will be used as an example in the following description. It should be understood however, that this example is, of course, not limiting, and the invention may also apply to other types of endocardial leads (for instance, a sensing/pacing lead in multiple sites of the right ventricle), or to pacing and/or sensing leads, electrodes of which are in contact with other tissues, nerves, muscles, etc.

The lead 10 is of the general type as described, for example, in U.S. Pat. No. 6,385,492 assigned to ELA Medical, S.A. In the vicinity of the distal tip 14 intended to be introduced in the coronary venous network, the lead body 12 comprises a plurality of electrodes 16, for example, ten electrodes as represented in FIG. 1. The lead also comprises an electronic circuit 20 mounted on a rigid ring 18. This electronic circuit is hermetically encapsulated while retaining biocompatibility with the surrounding body fluids and tissues. Similar to the microcables along the lead, the circuit can be incorporated within the lead body, or placed in a cavity thereof.

The circuit 20 is represented in further detail in FIG. 2. The circuit comprises a first chip 22 incorporating the electronic circuit as such (an application-specific integrated circuit or ASIC), and a second chip 24 with a series of switches, advantageously integrated as micro electromechanical systems (MEMS).

The circuit comprises two terminals, 26 and 28, hereinafter respectively referred to as "proximal terminal" and "distal terminal", which are connected to the two conventional proximal P and distal D poles of a distant bipolar pulse generator 30, via a microcable spreading along the whole length of the lead body, and a connector 32 connected to generator 30. The circuit also comprises ten electrode terminals 34, each connected by a microcable to a respective electrode 16 placed on the surface of the lead.

FIG. 3 represents the electrical diagram of circuit 22 and associated switches 24. FIG. 3 also illustrates the proximal 26 and distal 28 terminals, as well as the ten electrode terminals 34. For greater clarity of the figure, these terminals have been duplicated into two series of ten terminals at the top and bottom parts of FIG. 3, but it should be understood that the first terminal 34 of the top part is electrically connected to the first terminal 34 of the bottom series, and so on for the other nine respective terminals of each series.

Each electrode terminal 34 is connected to the proximal terminal 26 via a respective switch 36 and a common serial resistor 38. Similarly, each electrode 34 is also connected to the distal connector 28 via a respective switch 40 and a common serial resistor 42. The switches 36 and 40 are advantageously bistable components which require power only for operating a change of state, but do not require power to be maintained in one state or the other.

The switches 36 are commanded by respective signals $P_1 \ldots P_{10}$ delivered by a first decoding circuit 44; the switches 40 are similarly commanded by respective signals $D_1 \ldots D_{10}$ delivered by a second decoding circuit 46.

The circuit 22 comprises a power supply (not represented) for example comprising a diode followed by a capacitor eventually associated with a voltage regulator circuit, so as to rectify the signals received on the terminals 26 and 28 and store the corresponding energy in the capacitor.

The decoding circuits 44 and 46 comprise a logic to detect and analyze a series of logic pulses applied to the proximal terminal 26 and/or distal terminal 28 (signals P and D applied at the input of circuits 44 and 46). The coding is, for example, of the Manchester type, one high logic level (one) defined by a "10" sequence, and one low logic level (zero) defined by a "01" sequence, the duration of the "1" and "0" being equal, for instance 30 μsec. The circuits 44 and 46 also comprise a synchronization logic to reconstitute a clock signal based on a series of received logic pulses, the half-period of the clock being defined by the time interval separating two pulse edges.

Once the clock signal has been received, the circuits 44 and 46 measure the durations separating the low and high logic levels, and deduce therefrom an address determining the switch(es) 36 or 40 to be closed. Decoding the signal thus establishes a particular corresponding configuration wherein each electrode is either connected to the proximal terminal 26, or the distal terminal 28, or electrically isolated from these two terminals. Hence, the proximal terminal P of the pulse generator will be connected to one or more of the lead's ten electrodes, so as to allow a bipolar sensing/pacing operation. If only one terminal (P or D) of the generator is used, or if the generator comprises only one terminal, the generator will be able to operate in unipolar sensing/pacing or pseudo-bipolar mode, as the current loop would be closed by the patient's body up to the metal case of the generator.

The circuit 22 also comprises an overvoltage detector to protect the circuit's electronics in case of a defibrillation shock delivery, use of an electro-cautery device, etc. The overvoltage detector uses a comparator 48 to detect an electrical current $I_p$ higher than a given limit value, for example 100 mA, through resistor 38. If a current higher than this value is detected, then the output of comparator 48 is changed and a signal $P_0$ is applied to the circuit 44, triggering immediate opening of all switches 36. Likewise, a comparator 50 measures a current $I_d$ higher than a given limit value through resistor 42 and a signal $D_0$ is applied to circuit 46, triggering the immediate opening of all switches 40.

The circuit 22 also comprises a comparator 52, which is a fast analog circuit presenting a response time lower than 10 μs, used to detect a differential voltage higher than a given threshold, for example 500 mV, between the proximal terminal 26 and distal terminal 28. Notably, such a situation occurs, as explained by referring to the time diagrams in FIG. 4, when the proximal terminal 26 is connected to the ground by the generator, and the generator delivers a micropulse to distal terminal 28. The comparator 52 switches and applies a signal $P_x$ and $D_x$ to the decoder circuits 44 and 46, forcing all switches 36 and 40 to open.

Figure 4:
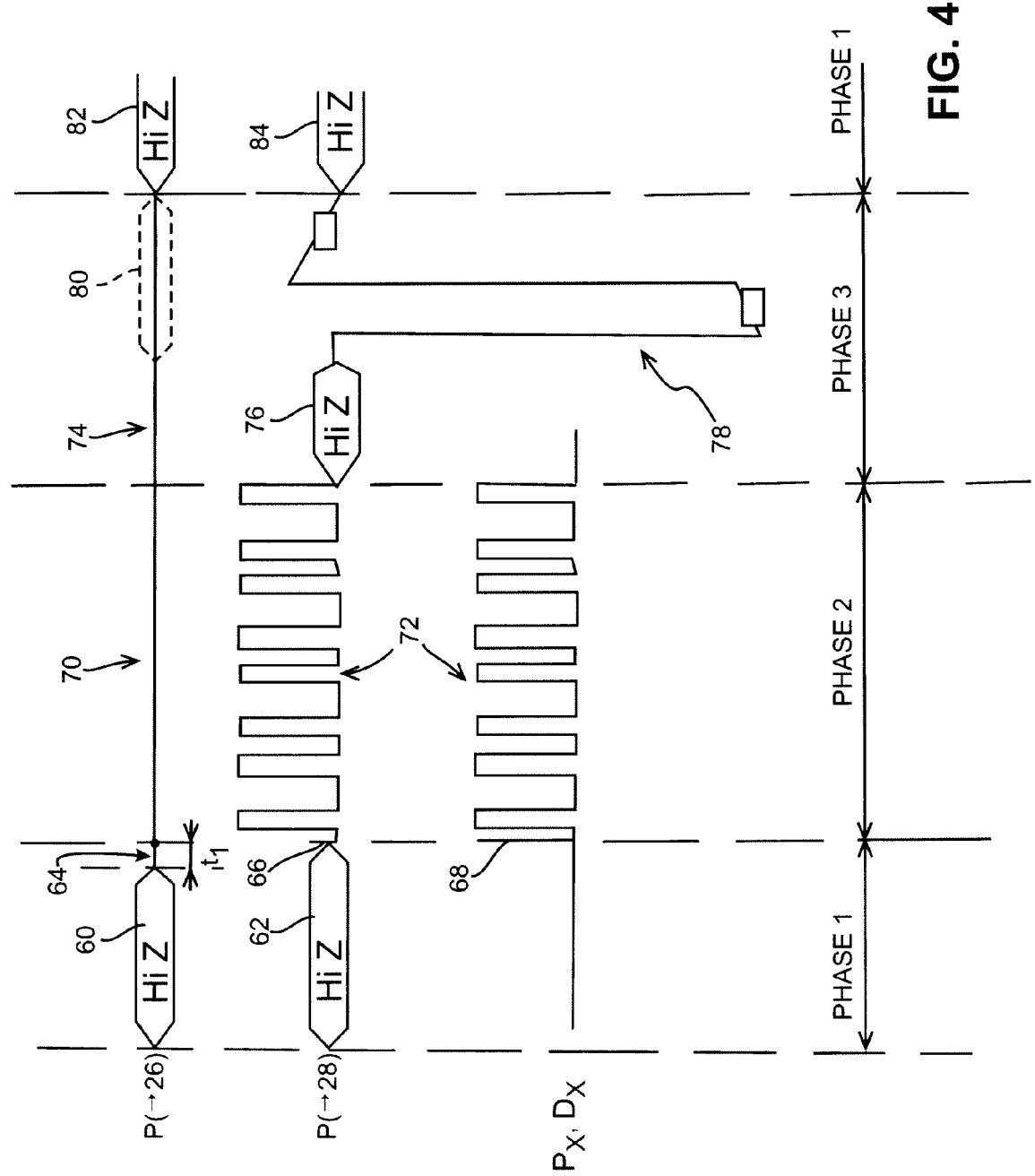
FIG. 4 is a set of time diagrams illustrating the operation of the circuit of this invention.

FIG. 4 represents the sequence of signals applied by the generator to the proximal terminal 26 and to the distal terminal 28, as well as the signal $P_x$, $D_x$ collected at the output of comparator 52.

Within a first phase (PHASE 1) corresponding to a period of inactivity of the device, the generator sets the proximal and distal P and D terminals of the generator in a high-impedance state (HiZ), as represented by references 60 and 62. Shortly before the end of this phase, the generator sets its proximal terminal to the ground, as represented by reference 64 (duration $t_1$). This state, corresponding to a zero logic state, will then be maintained until the application of the pacing pulse.

After the proximal terminal P has been set to zero, the case applies a micropulse 66 to the distal D terminal, constituting the beginning of the following phase (PHASE 2). The micropulse 66 has, for example, an amplitude of 0.5 V and a maximum duration of a few microseconds or fractions of microseconds. Due to the relatively low voltage and duration of the micropulse, the energy contained therein is very low, and, in any case, not high enough to present any risk to the patient. This micropulse is also applied to the electrode, or the electrodes, which is (are) connected to the distal terminal 28 of circuit 22 of the lead.

This micropulse is detected by the comparator 52, as shown in 68. The time required for the comparator to detect the micropulse and change the output state is very short, typically less than one microsecond, as the aim here is simply to schedule switching of a comparator, which is an operation that does not require any decoding or logic processing. During PHASE 2, detection of the micropulse induces the opening of all the switches 36 and 40 of the circuit. During this phase, the generator produces a sequence of coded pulses 72 designating which switch(es) will have to be connected either to the proximal terminal 26 or distal terminal 28 (the other switches remain open). Insofar as the proximal P terminal is always set to zero so as to be used as an electrical ground, as shown in 70, the series of coded pulses 72 collected on the distal terminal 28 is detected by the comparator 52 and remains identical at the output thereof, to be finally applied as such to the decoder circuits 44 and 46 (signals $P_x$ and $D_x$).

The following phase (PHASE 3) begins after receiving the coded signal 72, that forces closed the switch(es) designated by the coded pulses. During that period of time, the generator maintains the proximal terminal P as an electrical ground (as shown in 74), and sets the distal terminal D to a high-impedance level (as shown in 76).

The pacing pulse 78 can then be delivered. In the case of bipolar pacing, the proximal terminal P remains commuted to the ground (as shown in 74), whereas in case of unipolar pacing, the generator sets the proximal terminal P to a high-impedance level (as shown in 80). After delivery of the pacing pulse 78, the device returns to its inactive state. The proximal P and distal D terminals are set again to high impedance level by the generator (as shown in 82 and 84), and the switches remain in the previous state.

Figure 5:
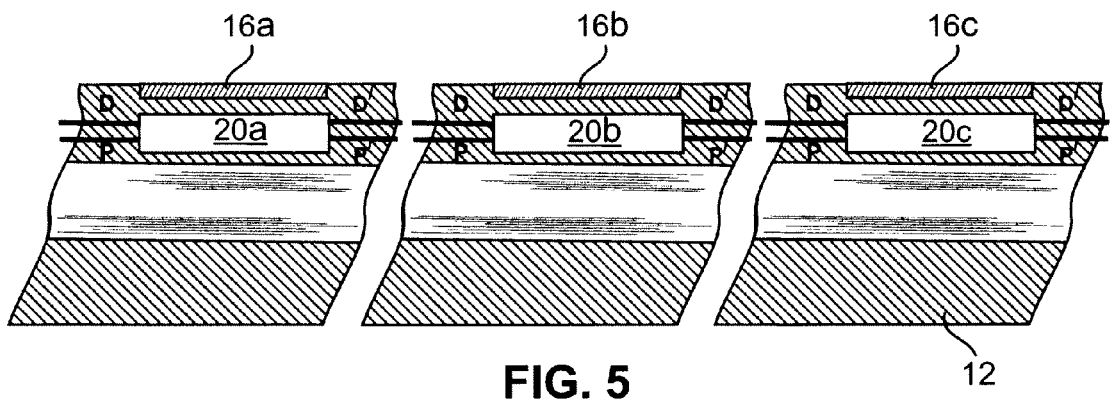
FIG. 5 is a detailed section view of the lead body in accordance with a first embodiments of this invention.
Figure 6:
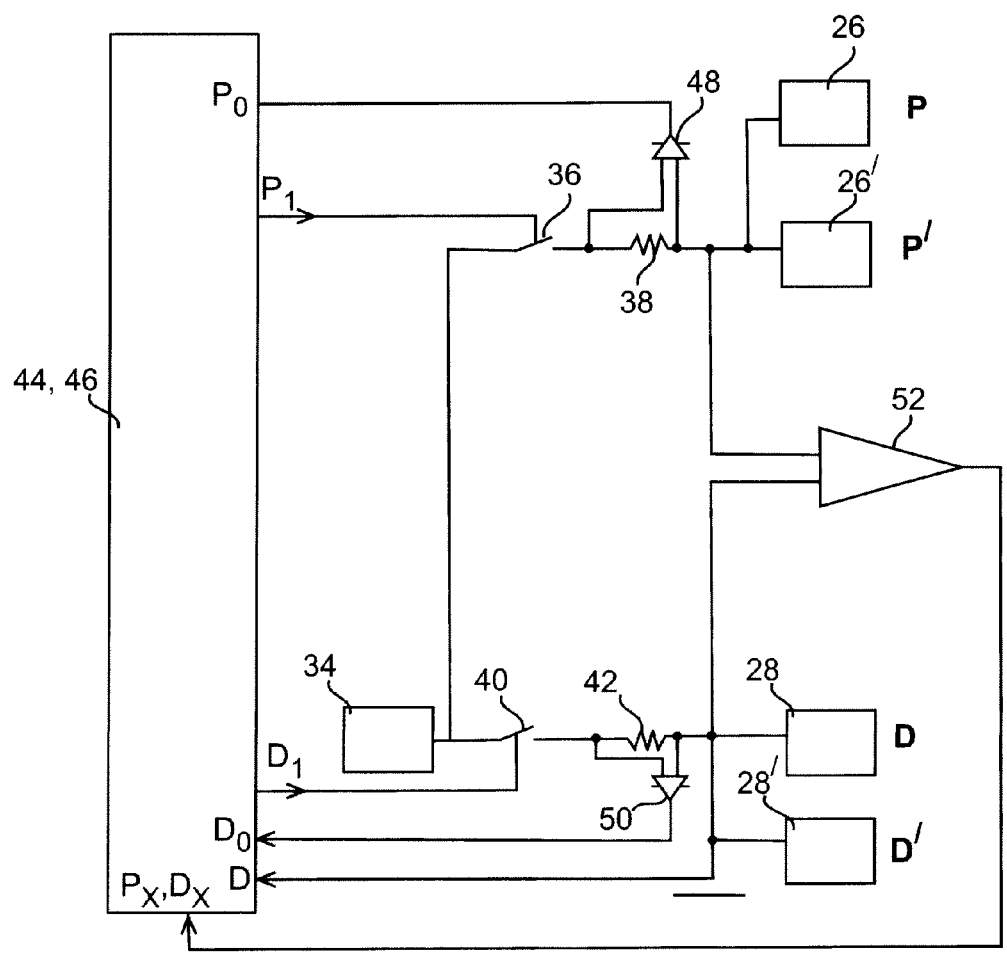
FIG. 6 is a schematic block diagram representing the main elements that constitute the circuit of this invention, for this example embodiment of the invention.

FIGS. 5 and 6 represent an alternative embodiment of the invention. In this alternative embodiment, the multiplexer/demultiplexer circuit 20 is split into a plurality of physically distinct sub-circuits 20a, 20b, 20c, . . . , placed in front of (i.e., in close proximity to) respectively corresponding electrodes 16a, 16b, 16c, . . . Each of these sub-circuits ensures addressing and decoding the associated electrode, and is incorporated in the wall layer of the body of the lead (12).

FIG. 6 represents the electrical diagram of such a sub-circuit. The same main elements as those of the circuits illustrated in FIG. 3 can be seen here, that is: a proximal terminal (26) and a distal terminal (28), decoding logic 44 and 46, overvoltage detectors 38 and 48 and 42 and 50, as well as a comparator 52 to decode the initial micropulse and successive changes of logic states of the command sequence.

In this particular embodiment, the sub-circuit is connected to only one electrode 34, and comprises only two switches 36 and 40: the first switch (36) connects the electrode terminal 34 to the proximal terminal 36, the second switch (40) connects the electrode terminal 34 to the distal terminal 38. Each sub-circuit integrates its own integrated circuit (44 and 46) for decoding, which ensures the selection of the corresponding electrode through controlled opening/closing of the associated switch 36 or 40.

Each of the sub-circuits comprises a second proximal terminal 26' and a second distal terminal 28', respectively electrically connected to terminals 26 and 28. These second terminals have a function of output terminals P' and D', for conducting the signals received on the proximal (P) and distal (D) input terminals to the following sub-circuit, that is: the sub-circuit located downstream towards the distal direction.

From the electrical point of view, the various sub-circuits 20a, 20b, 20c, etc. are each coupled to the microcables connected to the distal and proximal poles of the generator, and this configuration allows in particular, preventing too many microcables connected to the decoding circuit, as would be the case, should this circuit be common to plural electrodes, as in the case of FIG. 3.

One skilled in the art will appreciate that the present invention can be practiced by embodiments other than those disclosed, which are presented for purposes of illustration and are not limitation.

We claim:

1. A system for controlled commutation of multiplexed electrodes for an active implantable medical device, comprising
   a lead comprising electrodes adapted to be multiplexed and for sensing/pacing;
   at least one proximal terminal and/or distal terminal;
   a plurality of electrode terminals, wherein each electrode terminal is respectively coupled to an electrode adapted to be multiplexed and for sensing/pacing of the lead;
   a plurality of switches, wherein each switch has a closed position, in which a corresponding electrode terminal is connected to the proximal terminal and/or distal terminal, and an open position, in which a corresponding electrode terminal is isolated from the proximal terminal and/or distal terminal; and
   command means, comprising means for:
      receiving a modulated signal from a generator at the proximal terminal and/or the distal terminal, wherein the modulated signal comprises a coded series of logic pulses and a micropulse and contains switch configuration information of the plurality of switches;
      decoding the modulated signal to actuate the plurality of switches corresponding to a configuration of closed or open positions as identified by the modulated signal;
      detecting the micropulse within the received modulated signal, wherein the micropulse precedes the coded series, of logic pulses and has an amplitude and duration lower than the amplitude and duration of each of the coded series of logic pulses; and
      actuating, in response to the micropulse, the plurality of switches being in an open position over a duration at least equal to the duration of receiving the coded series of logic pulses.

2. The system of claim 1, wherein the means for detecting the micropulse further comprises a fast comparator presenting a response time shorter than 10 μs.

3. The system of claim 1 further comprising a plurality of distinct sub-circuits, each sub-circuit comprising an electrode terminal respectively connected to at least one of the sensing/pacing electrodes of the lead, at least one switch of the plurality of switches, wherein each sub-circuit includes its own command means.

4. A lead for an active implantable medical device comprising:
   an elongated body comprising at least one conductor,
   a connector connected to the at least one conductor and a proximal terminal and/or distal terminal of a generator,
   a plurality of multiplexed sensing/pacing electrodes, and
   a controlled commutation circuit selectively coupling or uncoupling each of the electrodes to the at least one conductor, the controlled commutation circuit comprising a plurality of switches,
   wherein the controlled commutation circuit receives from the generator a modulated signal comprising a coded series of logic pulses and micropulse and containing switch configuration information of the plurality of switches, and
   wherein the controlled commutation circuit actuates the plurality of switches corresponding to the switch configuration information identified by the modulated signal.

5. The lead of claim 4, wherein the connector is level with a first extremity of the elongated body and wherein the plurality of multiplexed sensing/pacing electrodes is level with a second extremity of the elongated body, and wherein the second extremity of the elongated body is positioned opposite from the first extremity of the elongated body.

6. The lead of claim 5, wherein the controlled commutation circuit is within the lead and is level with the second extremity and in the vicinity of the sensing/pacing electrodes.

7. The lead of claim 5, wherein the controlled commutation circuit comprises a plurality of distinct sub-circuits, each sub-circuit comprising an electrode terminal respectively connected to one of the sensing/pacing electrodes of the lead, a switch, or plurality of switches, associated with the electrode terminal, wherein each sub-circuit includes its own command means, and wherein the sub-circuits are each incorporated into the elongated body of the lead, in close physical proximity to a corresponding electrode, and coupled to the at least one conductor.

8. A generator for providing commands to a system for controlled commutation of multiplexed electrodes for an active implantable medical device, the generator comprising:
   means for delivering a modulated signal and a micropulse to a proximal terminal and/or distal terminal, of the system for controlled commutation of multiplexed electrodes,
   wherein the modulated signal comprises a coded series of logic pulses defining identifying a particular configuration for coupling the multiplexed electrodes to the proximal terminal and/or the distal terminal, and wherein the micropulse precedes the coded series of logic pulses and has an amplitude and duration lower than the amplitude and duration of each of the coded series of logic pulses.

9. The generator of claim 8 further comprises means for setting the proximal terminal and/or the distal terminal, to a high level of impedance prior to delivering the micropulse.

10. The generator of claim 9 further comprises:
means for setting one of the proximal terminal or the distal terminal to a state of high impedance, and;
means for setting the other terminal to the ground, prior to delivering the micropulse.

11. A generator producing a commutations command signal for an active implantable medical device, the commutation command signal comprising a modulated signal and the modulated signal comprising a coded series of logic pulses identifying a particular configuration for coupling lead electrodes to at least one proximal terminal and/or distal terminal of the generator, the modulated signal further comprising a micropulse, the micropulse preceding the coded series of logic pulses and presenting an amplitude and duration lower than the amplitude and duration of each of the logic pulses.

12. A system for controlled commutation of multiplexed electrodes for an active implantable medical device, comprising
a lead comprising a plurality of electrodes for sensing/pacing wherein said plurality of electrodes are multiplexed;
at least one proximal terminal and/or distal terminal;
a plurality of electrode terminals, wherein each electrode terminal is respectively coupled to one of said multiplexed electrodes for sensing/pacing of the lead;
a plurality of switches, wherein each switch has a closed position, in which a corresponding electrode terminal is connected to the proximal terminal and/or distal terminal, and an open position, in which a corresponding electrode terminal is isolated from the proximal terminal and/or distal terminal; and
command means, comprising means for:
receiving a modulated signal from a generator at the proximal terminal and/or the distal terminal, wherein the modulated signal comprises a coded series of logic pulses and a micropulse and contains switch configuration information of the plurality of switches;
decoding the modulated signal to actuate the plurality of switches corresponding to a configuration of closed or open positions as identified by the modulated signal;
detecting the micropulse within the received modulated signal, wherein the micropulse precedes the coded series of logic pulses and has an amplitude and duration lower than the amplitude and duration of each of the coded series of logic pulses; and
actuating, in response to the micropulse, the plurality of switches being in an open position over a duration at least equal to the duration of receiving the coded series of logic pulses.

13. The system of claim 12, wherein the means for detecting the micropulse further comprises a fast comparator presenting a response time shorter than 10 μs.

14. The system of claim 12 further comprising a plurality of distinct sub-circuits, each sub-circuit comprising an electrode terminal respectively connected to at least one of the sensing/pacing electrodes of the lead, at least one switch of the plurality of switches, wherein each sub-circuit includes its own command means.

* * * * *